(12) United States Patent
Haarer et al.

(10) Patent No.: US 8,267,576 B2
(45) Date of Patent: Sep. 18, 2012

(54) TIME-TEMPERATURE INDICATING DEVICE

(75) Inventors: Dietrich Haarer, Bayreuth (DE); Yoav Levy, Ramat Hasharon (IL)

(73) Assignee: Freshpoint Holdings SA, La Chaux-de-Fonds (CH)

( * ) Notice: Subject to any disclaimer, the term of this patent is extended or adjusted under 35 U.S.C. 154(b) by 274 days.

(21) Appl. No.: 11/666,886

(22) PCT Filed: Oct. 31, 2005

(86) PCT No.: PCT/EP2005/055645
§ 371 (c)(1),
(2), (4) Date: Dec. 4, 2007

(87) PCT Pub. No.: WO2006/048412
PCT Pub. Date: May 11, 2006

(65) Prior Publication Data
US 2008/0187021 A1    Aug. 7, 2008

(51) Int. Cl.
*G01K 3/00* (2006.01)
*G01K 3/04* (2006.01)
*G01K 7/00* (2006.01)
*G01D 21/00* (2006.01)
*G01K 1/02* (2006.01)
*G01N 31/00* (2006.01)
*G01N 31/22* (2006.01)

(52) U.S. Cl. ............ 374/102; 374/E3.004; 374/E7.001; 374/183; 436/2; 116/206; 116/216; 116/207; 422/400

(58) Field of Classification Search .................. 374/102; 436/2
See application file for complete search history.

(56) References Cited

U.S. PATENT DOCUMENTS

| | | | |
|---|---|---|---|
| 5,053,339 A * | 10/1991 | Patel | 436/2 |
| 5,667,303 A | 9/1997 | Arens et al. | 374/102 |
| 7,254,095 B1 * | 8/2007 | Braunberger | 368/327 |
| 7,290,925 B1 * | 11/2007 | Skjervold et al. | 374/106 |
| 7,785,894 B2 * | 8/2010 | Smolander et al. | 436/166 |
| 2006/0203882 A1 | 9/2006 | Makela et al. | 374/161 |

FOREIGN PATENT DOCUMENTS

| | | |
|---|---|---|
| EP | 0 276 335 | 8/1988 |
| EP | 276335 A1 * | 8/1988 |
| EP | 1645856 A1 * | 4/2006 |
| WO | 2004/077002 | 9/2004 |
| WO | WO 2004077002 A1 * | 9/2004 |

* cited by examiner

*Primary Examiner* — In Suk Bullock
*Assistant Examiner* — Jennifer Wecker
(74) *Attorney, Agent, or Firm* — Graeser Associates International Inc; Dvorah Graeser

(57) ABSTRACT

The present invention is generally in the field of measuring and indicating techniques and relates to a time-temperature indicating device and methods of manufacturing and reading this device. More specifically, the time-temperature indicator (TTI) device comprises at least one active reactant being at least a part of a component that is configured to be either an electrical component or transformable into an electrical component, said at least one active reactant being selected to be affectable by a chemical and/or physical reaction effecting a change in at least an electrical property of said electrical component at a rate that is time-temperature dependent.

12 Claims, 7 Drawing Sheets

TIME-TEMPERATURE INDICATING DEVICE

Figure 1A:
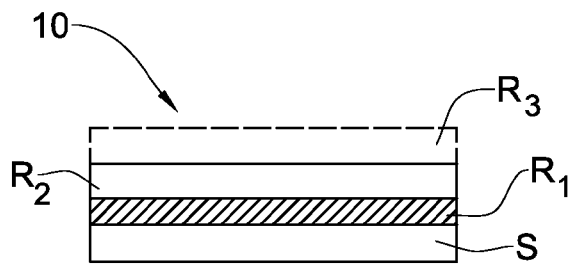

This invention is generally in the field of measuring and indicating techniques and relates to a time-temperature indicating device and methods of manufacturing and reading this device.

Time temperature indicators (alternatively called "time temperature integrators") are devices that are characterized by at least one changeable observable physical property that progresses in a rate that is proportional to the temperature and time, and thus provide an indication of the full or partial time-temperature history of their immediate surroundings. Time temperature indicators (TTIs) are simple and inexpensive devices, typically designed as labels. When attached to a perishable good, a TTI (appropriately designed and calibrated) monitors its time-temperature history and provides a simple, usually visual, straightforward summary of the exposure history of the product to time-temperature, thereby providing indication of the product freshness condition. Consequently, TTIs are among the most promising shelf-life-report technologies.

The TTI concept was developed to ensure the safety and quality of perishable goods, such as food and drug products, throughout their entire lifespan, from manufacturing to the time they are consumed by the end user. The safety and quality of many perishable goods such as food, drugs, vaccines and blood, depend mainly on appropriate storage conditions during distribution and storage. Different factors such as gas composition, relative humidity and temperature affect their real lifetime. The fact that changing conditions affect the effective shelf life of these kinds of goods is not reflected by a "best before . . . " type label that relies on appropriate storage conditions. Of all storage factors, temperature abuse is the most frequently observed factor for deterioration, based on diverse physical, chemical, enzymatic or microbial processes. Therefore, the TTI technology can provide a simple tool for controlling the food and drug chain. The color and/or other visual physical properties of the TTI varies as a function of the time at a rate which is temperature dependent, thus providing an active scale of "freshness" of the product to which it is attached, by comparing the color (or darkness) or any other varying visual property of the TTI label with a given comparative scale. Since the TTI indicators may be designed to provide a distinct "Yes" or "No" type of answer regarding the time temperature factor, they may provide an important "clear cut" answer and save further elaborate data inspection. This is ideal for HACCP (Hazard Analysis Critical Control Point), where the emphasis is on real time decision making and action.

Various TTIs are disclosed for example in the following patent publications:

U.S. Pat. No. 4,737,463 discloses a photoactivatable time-temperature indicator based on diacetylenic salts. A thermally unreactive ("inactive") diacetylenic salt (or a mixture of such salts) is mixed, in a polymeric matrix, with a material that generates acid upon exposure to light. Photoexcitation, preferably by UV or near UV light, causes the formation of a thermal reactive ("active") free diacetylenic acid. Following this activation step, a progressive color development occurs at a rate that increases with temperature. The indicator is useful for monitoring the freshness of perishable products, particularly those that require refrigeration.

WO 99/39197 discloses a technique, which provides a substrate for packaging time- and temperature-sensitive products for or for application thereon. According to this technique, planar time-temperature integrator is used consisting of a matrix and at least one reversible indicator embedded therein being arranged in the area of the substrate. The indicator has photochromic properties.

U.S. Pat. No. 6,435,128 discloses a time-temperature integrating indicator device that provides a visually observable indication of the cumulative thermal exposure of an object. The device includes a substrate having a diffusely light-reflective porous matrix and a backing. The backing includes on its surface a viscoelastic indicator material for contacting the substrate and a barrier material for substantially inhibiting the lateral and longitudinal flow of viscoelastic indicator material between the substrate and the backing.

U.S. Pat. No. 6,042,264 discloses a time-temperature indicator device, designed as a label, for measuring the length of time to which a product has been exposed to a temperature above a pre-determined temperature. The period of time of exposure is integrated with the temperature to which the indicator is exposed. The label is a composite of a plurality of layers adapted to be adhered at its underside to a product container. The label includes a printable surface layer, a longitudinal wicking strip that is adhered underneath the surface layer substantially at the opposite extremities only of the wicking strip and a lower substrate layer forming an envelope with said surface layer. A heat-fusible substance, which melts and flows above a pre-determined temperature, is applied on the surface of the wicking strip contiguous to at least one of the ends of the wicking member. When the heat-fusible substance is exposed to a temperature above the pre-determined temperature, the heat-fusible substance flows along the length of the wicking member. The label has a printable surface layer and is sealed at its peripheral edge to the peripheral edge of the substrate layer. These layers encapsulate the wicking member and the heat-fusible substance. The surface layer is provided with a sight window at an intermediate location over the wicking member through which the progress of flow on the wicking member is observed.

WO 03/077227 discloses a time indicating label comprising a label substrate having first and second surfaces, an acid-based indicator composition, and an activator composition. One of the acid-based indicator composition and the activator composition is on the first surface of the substrate, and both of these compositions when brought in contact remain adhered. The label may have a pressure sensitive adhesive on the second surface of the label. The label provides an effective means for determining the safety of frozen foods. The labels also provide a means of providing security by providing name badges that are time sensitive and may not be reused. The name badges provide a means to monitor the length of a visitor's time and prevent reusing the name badge.

WO 03/044521 discloses a sensor adapted to be remotely readable by RF techniques for identification of the quality of a packaged foodstuff. The sensor either reacts with compounds generated in the atmosphere of the foodstuff package due to the microbiological decay of the foodstuff, for example hydrogen sulfide or other sulfide compounds, or the sensor is responsive to an increased oxygen content in the atmosphere of the package due to a leakage in the package. The sensor is based on a RF circuit. Oxygen or the microbiologically generated gas affects the electrical properties of the circuit material. For example, the resistor, the capacitor or the inductive coil of the circuit or at least a fraction thereof are made of silver, iron, aluminum, a redox-type indicator-dye, a conductive polymer, or copper. Due to the reaction of the aforementioned gases with these materials, the sensor resistance, conductivity, capacitance and/or inductance of the respective sensor elements changes depending on the amount of the disintegrating gas.

WO 01/25472 discloses a biosensor useful to monitor the time and temperature to which a product has been exposed. The biosensor is based on a RF circuit comprising a unit, which changes its conductivity/resistance as a function of time and temperature. This unit comprises an enzyme and a substrate, wherein the enzyme is adapted to affect the substrate so that its conductivity increases as a function of time and temperature. Thus, a biosensor is disclosed, whose RF circuit can be activated by applying, for instance, a magnetic field over the same to generate a measurable current, which is dependent on the total resistance of the circuit and which thus varies as a function of the time and temperature to which the unit of the biosensor has been exposed.

WO 95/33991 discloses a condition indicator for perishable goods. The indicator comprises sensor means for gas or vapour associated with decay or contamination affecting an electrical property of said sensor means, which are incorporated into an electrical circuit measuring said property. The electrical circuit disclosed in WO 95/33991 is not a RF circuit. That means the sensor changes are not remotely readable. The circuit may be printed. The sensor may comprise a semiconducting material such as polypyrroles, which change an electrical property such as resistance or impedance on exposure to certain gases.

There is a need in the art to facilitate continuous and partial temperature control along food (and other perishable goods) supply chains, by providing an improved TTI device and methods of its manufacture and use.

To date, many countries have well-established regulations and/or recommendations for compliance of the temperature during the chill chain. To control and monitor the temperature along the chill chain one takes, up to now, only a few spot tests of presumably representative samples. This is limited, at most, to the part of the chill chain that is between the producer and the backyard of the final distributor. The part of the chill chain that concerns the end user is, in most cases, not monitored at all. Thus, there is still no well-established continuous temperature control along the food chain.

The present invention solves the above problem by providing a TTI device that is capable of providing a simple summary of the time and temperature history of any good to which it is coupled. The TTI device of the present invention is configured so as to provide a change in the electrical properties of a TTI structure induced by a time-temperature dependent chemical and/or physical process in the TTI structure. This change is detectable as a change in one or more properties of the radiation coming from the TTI structure, such as emission or reflection. This may be radiation that is intrinsically generated by the TTI device, relaying on internal energy resources such as batteries, in the case it is configured as a so-called "active structure", or radiation that is produced by the TTI structure as a response to a certain external field in the case of a "passive" TTI structure. Alternatively or additionally, the TTI structure may be configured to provide a change in an electric conductivity through a component of the TTI structure. This component may be initially an electrically conductive component that changes its conductivity as a function of the temperature and the time. Alternatively, such a component may be of a considerably nonconductive character, and the electrical conductivity may be induced and changed as a function of the temperature and the time, upon transferring the component into an electrically conductive one. The change in electrical properties of the TTI structure may also be visually detectable, as a change in the optical properties of the TTI, such as color (e.g., as a result of penetration of a viscoelastic liquid into a porous medium, doping processes of a semiconductor), reflectivity, etc.

Hence, the present invention relates in its broadest aspect to a time-temperature indicator device comprising at least one active reactant being at least a part of an electrical component, said at least one active reactant is selected such it intrinsically changes at least an electrical property of said electrical component at a rate that is time-temperature dependent.

In another aspect, the present invention relates to a time-temperature indicator device comprising (i) at least one active reactant being at least a part of an electrical component, said at least one active reactant being selected to be affectable by a chemical and/or physical reaction effecting a change in at least an electrical property of said electrical component at a rate that is time-temperature dependent; and (ii) at least one first passive reactant in the form of a viscous substance, said chemical and/or physical reaction being a reaction between said at least one active reactant and said at least one first passive reactant and wherein said at least one first passive reactant is selected such that it causes time-temperature dependent development of said chemical and/or physical reaction.

In yet another aspect, the present invention also relates to a time-temperature a time-temperature indicator device comprising (i) at least one active reactant being at least a part of an electrical component, said at least one active reactant being selected to be affectable by a chemical and/or physical reaction effecting a change in at least an electrical property of said electrical component at a rate that is time-temperature dependent; (ii) at least one first passive reactant in the form of a viscous substance; and (iii) at least one second passive reactant wherein said chemical and/or physical reaction is a reaction between said at least one active reactant and said at least one second passive reactant and wherein said at least one first passive reactant is selected such that it causes time dependent transfer of heat towards said at least one second passive reactant thereby causing time-temperature dependent development of said chemical and/or physical reaction.

Generally, the TTI structure is configured to define at least one component (e.g., capacitor, resistor, diode, inductance coil, RF circuit or an active or passive antenna), the electrical properties of which are changed as a result of the time and temperature dependent physical and/or chemical process. This change may consist of but is not limited to one of the following: decreased reflectivity signal from an electrically conductive component as a result of time and temperature dependent disintegration of an electrically conductive material of said component (e.g., a change in homogeneity); decreased electric current through the component as a result of a change in a dielectric layer thereof; appearance and/or increase of electrical conductivity of an initially non-conductive layer thereof; a change of Q-factor of the device, a change in the resonance frequency of an electrical circuit as a result of time and temperature dependent disintegration of an electrically conductive material of the circuit.

The technology of the present invention relies on a physical and/or chemical reaction taking place in at least one reactant. This may be reaction of this reactant with itself. Preferably, the reaction takes place between at least two reactants. These reactants may be located adjacent to one another (e.g., space-localized at the initial conditions) or may be in the form of a reactive mixture. At least one of the reactants is directly exposed to the time and temperature variations.

It should be understood that, when at least two reactants are involved, the TTI structure itself may include at least one of the at least two reactants needed for the required process, while the other reactant(s) may "come" from the environment (e.g., oxygen that is present in the air). This at least one reactant to be in the TTI structure is termed "active reactant", and is the one that induces or undergoes said changeable electrical property in the device and/or component with which the reactant is associated.

Hence, the construction may be such that the active reactant is directly exposed to the time and temperature changes. Alternatively, the at least one other reactant (termed "passive reactant") is directly exposed to such changes. In this connection, it should be noted that the term "directly exposed" as used herein with respect to the passive reactant refers to a relative condition of the passive reactant as compared to the active one, while the passive reactant may by itself be affected by the time and temperature changes of the surroundings via another "passive" reactant. It should be noted that in most real applications of the present invention, all the reactants of the TTI structure are more or less evenly exposed to the temperature changes.

The term "active reactant", as compared to a "passive" reactant, signifies a reactant forming, undergoing or being a part of the TTI component of a changeable electrical property. The active reactant may be initially electrically conductive; or transformable into an electrically conductive material; or may be a dielectric material of an electrical component, such that changes in a dielectric permeability of this dielectric material (caused by time and temperature dependent reaction/process) affect the electrical property of the electric component.

As indicated above, the physical and/or chemical reaction (process) may be involving, mediated, catalyzed, inhibited and/or induced by additional one or more substances (passive reactant(s)). The passive reactant(s) may for example include a viscous substance (termed here "viscoelastic component") that initiates diffusion of the passive and active reactants to one another at a rate that is correlated to the time and temperature. Alternatively, a viscous substance, being a dielectric material, may present the active reactant of the TTI structure, as for example in the case of a capacitor electric component: the viscoelastic substance fills a porous dielectric spacer that is located in between the capacitor plates, and the degree of penetration of this viscoelastic liquid, being a function of the elapsed time-temperature, changes the capacitance. Similarly, the active component may be composed of several capacitors, the time-temperature history being expressed in the number of capacitors that have been penetrated and thus "destroyed" by the viscoelastic liquid.

It should be noted that a "viscous substance" may be a viscous liquid or polymer. The term "viscoelastic component" used herein refers also to such a viscous substance. As indicated above, for generating a time-temperature dependent radiation from the TTI that is correlated to the time-temperature history, the active reactant(s) may include an electrically conductive material (metal or semiconductor), the electrical conductivity of which may be affected as a result of doping or dedoping; or may include a material that is transformable into an electrically conductive material (e.g. an organic semiconductor, such as polythiophene derivative, that is transformed into an organic conductor by a reaction with a dopant, such as iodine), or may be a dielectric material forming a part of an electric component (e.g., a dielectric spacer of a capacitor). It should be understood that common to all these examples, is a change in electrical property of the TTI structure.

Thus, the present invention provides a time-temperature indicator (TTI) device comprising at least one active reactant being at least a part of a component that is configured to be either an electrical component or transformable into an electrical component, said at least one active reactant being selected to be affectable by a chemical and/or physical reaction effecting a change in at least an electrical property of said electrical component at a rate that is time-temperature dependent.

The electrical component may be configured to operate as a resistor, and/or a capacitor, and or an RF circuit and or any other electrical element/circuit.

Preferably, the chemical and/or physical reaction is induced by at least one passive reactant.

According to a preferred embodiment of the invention, the TTI device comprises at least two reactants located adjacent to each other (e.g., in contact with one another), wherein these at least two reactants are selected such that when at least one passive reactant from said at least two reactants at least partially undergoes a phase change it effects the chemical and/or physical reaction with at least one active reactant from said at least two reactants, said chemical and/or physical reaction effecting a change in an electrical property of a component with which said at least one active reactant is associated.

It should be understood that the term "at least partly undergoes a phase change" used herein signifies local, partial or complete sublimation, or melting, or dissolution, or material penetration, or any of first, second and mixed order phase transition, such as glass transition, melting, etc.

As indicated above, the device may include a viscoelastic component as a second "passive" reactant, which may be at the outer surface of the device; or may present the "active" reactant. The viscoelastic component may or may not have a solid-to-liquid transition at temperatures that are relevant to the specific application and consequently monitor partial or full time temperature history. The viscoelastic component is characterized by that when being exposed to temperatures higher than a certain threshold temperature specific for said viscoelastic component, it undergoes a change in its mobility and ability to dissolve and transport other chemical substances and propagate in porous solids. This certain temperature (freezing point) may be selected to be within a temperature range relevant for a specific application of a TTI device and thus the use of this viscoelastic component provides for partial time-temperature history indication: below this temperature, there is no measurement of time-temperature changes at all, e.g., since the viscoelastic component is a solid and has no time-temperature dependence. Alternatively, the viscoelastic component may be selected with such a threshold temperature lower than the relevant temperature range thus providing for full time-temperature history measurements. Considering the viscoelastic substance as a first "passive" reactant, such a change in its mobility causes a phase change process in the second passive reactant thereby causing time dependent development of said chemical and/or physical reaction between the active and second passive reactants.

Considering a capacitor component formed by two metal/semiconductor layers that are separated by a porous solid having a certain dielectric constant, a viscoelastic component may be used as a passive reactant to penetrate the porous component at a rate that is temperature dependent and thereby cause either a sudden short in the capacitor or a gradual change in the capacitance due to the difference in the dielectric constants of the pure porous solid and the porous solid filled with the viscoelastic component.

The TTI device is appropriately designed to prevent the physical and/or chemical reaction when the device is inoperative, and allow the development of this process/reaction when the device is put in operation. This may be achieved by initially placing the entire TTI structure in a sealed enclosure, which is configured to allow breaking, removing or puncturing thereof to thereby expose the TTI structure to the environmental changes. Another option is to use an adhesive-type viscoelastic polymer or placing a viscoelastic polymer on a label, thus attaching the viscoelastic component to the other part of the TTI (active reactant, or active and passive reactants), which is inactive without the viscoelastic component. Yet another option is to place a passive reactant (e.g., viscoelastic component) in a separate from the active reactant sealed reservoir, and when the TTI device is to be put in operation, removing the sealed enclosure and attaching the reservoir to the other part of the TTI (active reactant, or active reactant and a second passive reactant) to thereby allow penetration of the passive reactant (e.g., viscoelastic component) from the reservoir to the other part of the TTI. In yet another embodiment, the TTI device, while being inoperative, is kept at a temperature in which the TTI structure (i.e., active reactant(s) and possibly also passive reactant(s)) is either inactive or substantially inactive; and to put the device in operation, it is exposed to the relevant temperature range.

As indicated above, the active reactant may be an electrically conductive material within an electric circuit. The electrically conductive material may be patterned to form the features of an RF tag (antenna, resistor or capacitor). The chemical and/or physical reaction thus causes time dependent changes in the resonance circuit of the tag (which with time might result in breaking the circuit). The RF circuit pattern may be produced by any known suitable technique, e.g., printing (e.g., ink jet printing), CVD, PVD, sputtering, patterning (e.g., molding and cutting/etching), etc. The device may be configured as a multi-layer structure (hybrid structure), including a first substrate layer of an electrically insulting (and preferably optically transparent) material, carrying a second layer structure of a component formed by said active reactant (electrically conductive layer; or a layer structure patterned to form a capacitor or RF tag), and possibly also a third layer of passive reactant material. On top of said passive reactant layer structure, another layer of a passive reactant (e.g., viscoelastic component) may be provided. The device may also include an uppermost layer of an optically transparent and electrically insulating material.

Preferred time-temperature indicator devices according to the present invention are characterized in that the electrical component is selected from the group consisting of resistor, capacitor, diode, inductance coil and antenna. It is especially preferred that the electrical component is configured as at least one element of an RF circuit.

Also preferred are time-temperature indicator devices, wherein the chemical and/or physical reaction is selected from the group consisting of acid-base reaction, oxidation-reduction reaction and salt forming reaction.

Preferred time-temperature indicator devices include those, wherein said at least one active reactant is a polymer transformable from its initial non-electrically conductive state to an electrically conductive state. It is even more preferred when the at least one active reactant is polythiophene and the passive reactant is iodine, or alternatively when the at least one active reactant is polyaniline and the passive reactant is a peroxydisulfate species.

The time-temperature indicator devices according to the present invention preferably comprise a capacitor as the electrical component and it is even more preferred when said capacitor is configured as an element of an RF circuit and wherein the at least one active reactant is a dielectric material presenting a dielectric spacer in said capacitor.

Time-temperature indicator devices are preferred, wherein the chemical and/or physical reaction consists of mixing the at least one active reactant and the at least one first passive reactant, thereby causing a change in permeability of the at least one active reactant.

It is also preferred when the time-temperature indicator device according to present invention is configured as a multilayer structure, including a substrate layer of an electrically insulting material, carrying a layer structure configured to form the electrical component. It is especially preferred when the layer structure comprises first and second electrode layers spaced by a dielectric layer, thereby forming the capacitor-type electric component.

More preferably, the time-temperature indicator device is configured as a two-part device, wherein one of the two parts includes at least the at least one active reactant, and the other part includes the at least one first and/or second passive reactant, the two parts being configured to be attachable to one another to thereby induce the chemical and/or physical process and thereby put the device in operation.

The present invention also provides a method of manufacturing a time-temperature indicating device. The method comprises: selecting at least one material for at least one reactant to be a part of a component that is either an electrical component or transformable into an electrical component, said at least one reactant being selected so as to be affectable by a chemical and/or physical process effecting a change in an electrical property of said component; and incorporating said component into the TTI device.

Preferably, at least one passive reactant is also selected to be incorporated in the TTI structure, for example being located adjacent to the active reactant. This internal passive reactant is of the kind undergoing a phase change, and thus effects a chemical or physical reaction with the active reactant located adjacent thereto, said chemical or physical reaction effecting a change in an electrical property of a component with which the active reactant is associated.

According to one embodiment, the method also comprises selecting a viscoelastic component as an additional passive reactant; and arranging the reactants and the viscoelastic component so as to provide contact between the reactants and to locate viscoelastic component at an outer surface of the device to be exposed to the environmental changes. According to another embodiment, the viscoelastic component is selected to be the active reactant, and the TTI structure is constructed by arranging a viscoelastic layer between two conductive layers and exposing the viscoelastic layer to the environmental changes. The viscoelastic material has a certain temperature such that the mobility and viscosity thereof change as a function of time when said viscoelastic component is exposed to a temperature higher than said certain temperature.

Thus, the method of time temperature indication according to the present invention comprises the step of a chemical and/or physical reaction between at least one active reactant and at least one passive reactant in the form of a viscous substance effecting a change in at least an electrical property of an electrical component wherein said at least one active reactant is at least a part of a component that is configured to be either an electrical component or transformable into an electrical component and wherein said at least one passive reactant is selected such that, when being exposed to a temperature higher than a certain temperature specific for said at least one passive reactant, causing time-temperature dependent development of said chemical and/or physical reaction.

Even more preferred is said method of time temperature indication, wherein said at least one passive reactant effects time dependent transfer of heat towards at least one second passive reactant thereby causing time-temperature dependent development of said chemical and/or physical reaction between said at least one active reactant and said at least one second passive reactant effecting a change in at least an electrical property of an electrical component wherein said at least one active reactant is at least a part of a component that is configured to be either an electrical component or transformable into an electrical component.

Another embodiment of the present invention relates to a printing ink or printing ink concentrate, comprising the at least one active reactant, the at least one first passive reactant and/or the at least one second passive reactant of the above-described time-temperature indicator devices.

Yet another embodiment of the present invention relates to a packaging material or a label, comprising at least one of the above-described time-temperature indicator devices.

At a glance, the present invention relates to the following aspects:

In a first aspect, the present invention relates to a time-temperature indicator (TTI) device comprising at least one active reactant being at least a part of a component that is configured to be either an electrical component or transformable into an electrical component, said at least one active reactant being selected to be affectable by a chemical and/or physical reaction effecting a change in at least an electrical property of said electrical component at a rate that is time-temperature dependent.

Preferably, said device is characterized in that said electrical component includes at least one of the following: resistor, capacitor, diode, inductance coil, and antenna.

Preferably, said device is characterized in that said electrical component is configured as at least one element of an RF circuit.

Preferably, said device is characterized in that said electrical component is configured as an RF circuit.

Preferably, said device is characterized in that said active reactant is an electrically conductive material. More preferably, said device is characterized in that said active reactant is an electrode in the electrical component configured as a capacitor. More preferably, said device is characterized in that said active reactant is an element of the electrical component configured as an RF circuit.

Preferably, said device is characterized in that said active reactant is configured as an RF circuit.

Preferably, said device is characterized in that said chemical and/or physical reaction includes oxidation-reduction reaction.

Preferably, said device is characterized in that said active reactant is a dielectric material presenting a dielectric spacer of the capacitor-type electric component, said chemical and/or physical reaction causing a change in permeability of the active reactant.

Preferably, said device is characterized in that said active reactant is a polymer transformable from its initial non-electrically conductive state to an electrically conductive state.

Preferably, said device is configured as a multi-layer structure, including a substrate layer of an electrically insulting material, carrying a layer structure configured to form said at least one component. More preferably, said device is characterized in that said layer structure comprises an electrically conductive layer forming at least a part of at least one of the following: a resistor component, capacitor component, diode component, inductance coil component, and an RF circuit component. Even more preferred is a device, wherein said layer structure comprises first and second electrode layers spaced by a dielectric layer, thereby forming the capacitor-type electric component.

Preferably, said device has a sealed enclosure configured to be at least partly removed to thereby expose the at least one reactant to the temperature changes.

In a second aspect, the present invention relates to a time-temperature indicator (TTI) device comprising at least one active reactant being at least a part of a component that is configured to be either an electrical component or transformable into an electrical component, said at least one active reactant being selected to be affectable by a chemical and/or physical reaction effecting a change in at least an electrical property of said electrical component at a rate that is time-temperature dependent, wherein said device comprises at least one passive reactant, said chemical and/or physical process being a reaction between the active reactant and said at least one passive reactant.

Preferably, said device is characterized in that said electrical component includes at least one of the following: resistor, capacitor, diode, inductance coil, and antenna. More preferably, said device comprises an array of the capacitor components.

Preferably, said device is characterized in that said electrical component is configured as at least one element of an RF circuit.

Preferably, said device is characterized in that said electrical component is configured as an RF circuit.

Preferably, said device is characterized in that said active reactant is an electrically conductive material. More preferably, said device is characterized in that said active reactant is an electrode in the electrical component configured as a capacitor. More preferably, said device is characterized in that said active reactant is an element of the electrical component configured as an RF circuit.

Preferably, said device is characterized in that said active reactant is configured as an RF circuit.

Preferably, said device is characterized in that said at least one passive reactant is a dielectric spacer of a capacitor of the electrical component.

Preferably, said device is characterized in that said at least one passive reactant includes a salt. More preferably, said device is characterized in that said chemical and/or physical reaction consists of mixing of the active reactant and the salt, thereby affecting homogeneity of the active reactant material. Even more preferably, said device comprises a second passive reactant in the form of a viscous substance, selected such that, when being exposed to temperature higher than a certain temperature specific for said viscous substance, allows time dependent transfer of heat towards the salt thereby causing time-temperature dependent development of said mixing.

Preferably, said device is characterized in that said at least one passive reactant includes a viscous substance, selected such that, when being exposed to temperature higher than a certain temperature specific for said viscous substance, causing time-temperature dependent development of said chemical and/or physical reaction. More preferably, said device is characterized in that said viscous substance is selected such that said certain temperature lies within a predetermined temperature range relevant for a specific application of the device, the device being thereby operable for partial time-temperature history indication. More preferably, said device is characterized in that said viscous substance is selected such that said certain temperature lies within a predetermined temperature range relevant for a specific application of the device, the device being thereby operable for full time-temperature history indication.

Preferably, said device comprises a second passive reactant in the form of a viscous substance, selected such that, when being exposed to temperature higher than a certain temperature specific for said viscous substance, allows time dependent transfer of heat towards the first passive reactant thereby causing time-temperature dependent development of said chemical and/or physical reaction. More preferably, said device is characterized in that said viscous substance is selected such that said certain temperature lies within a predetermined temperature range relevant for a specific application of the device, the device being thereby operable for partial time-temperature history indication. More preferably, said device is characterized in that said viscous substance is selected such that said certain temperature lies within a predetermined temperature range relevant for a specific application of the device, the device being thereby operable for full time-temperature history indication.

Preferably, said device is characterized in that said chemical and/or physical reaction includes at least one of the following: acid-base reaction, oxidation-reduction reaction, and salt forming reaction.

Preferably, said device is characterized in that said chemical and/or physical reaction is an oxidation-reduction reaction, said at least one passive reactant being a substance from the surroundings of the device.

Preferably, said device is characterized in that said active reactant is a dielectric material presenting a dielectric spacer of the capacitor-type electric component, said chemical and/or physical reaction causing a change in permeability of the active reactant.

Preferably, said device is characterized in that said active reactant is a polymer transformable from its initial non electrically conductive state to an electrically conductive state. More preferably, said device is characterized in that said active reactant is polythiophene, and the passive reactant is iodine. More preferably, said device is characterized in that said active reactant is polyaniline, and the passive reactant is a peroxydisulfate species.

Preferably, said device is configured as a multi-layer structure, including a substrate layer of an electrically insulting material, carrying a layer structure configured to form said at least one component.

More preferably, said device is characterized in that said layer structure comprises an electrically conductive layer forming at least one of the following: a resistor component, capacitor component, diode component, inductance coil component, and an RF circuit component. Even more preferred is a device that comprises an array of capacitor components.

More preferably, said device is characterized in that said layer structure comprises the first passive reactant, which is selected to induce the time-temperature dependent chemical and/or physical process, and is located above the active reactant. Even more preferred is a device, wherein said layer structure comprises a second passive reactant, in the form of a viscous substance, selected such that, when being exposed to temperature higher than a certain temperature specific for said viscous substance, allows time dependent transfer of heat towards the first passive reactant thereby causing time-temperature dependent development of said chemical and/or physical reaction. Most preferred is a device, wherein said viscous substance is located on top of the active reactant, which covers the first passive reactant. Most preferred is a device, wherein said viscous substance is located on top of the first passive reactant, which is located on top of the active reactant.

More preferably, said device is characterized in that said layer structure comprises the first passive reactant, which is selected to induce the time-temperature dependent chemical and/or physical process, and is located above the active reactant. Even more preferred is a device, wherein said layer structure comprises a second passive reactant, in the form of a viscous substance, selected such that, when being exposed to temperature higher than a certain temperature specific for said viscous substance, allows time dependent transfer of heat towards the first passive reactant thereby causing time-temperature dependent development of said chemical and/or physical reaction. Most preferred is a device, wherein said viscous substance is located on top of the active reactant, which covers the first passive reactant. Most preferred is a device, wherein said viscous substance is located on top of the first passive reactant, which is located on top of the active reactant.

More preferably, said device is characterized in that said layer structure comprises first and second electrode layers spaced by a dielectric layer, thereby forming the capacitor-type electric component. Even more preferred is a device, wherein said at least one passive reactant includes a viscous substance, selected such that, when being exposed to temperature higher than a certain temperature specific for said viscoelastic component, penetrates into the dielectric spacer layer thereby causing time-temperature dependent development of said chemical and/or physical reaction.

Preferably, said device is configured as a two-part device, wherein one of the two parts includes at least the active reactant, and the other part includes the passive reactant, the two parts being configured to be attachable to one another to thereby induce said chemical and/or physical process and thereby put the device in operation. More preferably, said device is characterized in that said one part includes the active reactant and the first passive reactant, and the other part includes the second passive reactant. More preferably, said device is characterized in that said other part includes the passive reactant in the form of a viscous substance, selected such that, when being exposed to temperature higher than a certain temperature specific for said viscoelastic component, is capable of causing time-temperature dependent development of said chemical and/or physical reaction. More preferably, said device is characterized in that said other part containing the passive reactant has a sealed enclosure configured to be at least partly removed to thereby expose said passive reactant to the temperature changes.

In a third aspect, the present invention relates to a time-temperature indicator (TTI) device comprising at least one active reactant in the form of an electrically conductive layer patterned to form at least one element of an RF circuit component, said at least one active reactant being selected to be affectable by a chemical and/or physical reaction effecting a change in a signal generated by the RF circuit at a rate that is temperature dependent.

In another aspect, the present invention relates to a time-temperature indicator (TTI) device comprising at least one active reactant and at least one passive reactant, said at least one active reactant being in the form of an electrically conductive layer patterned to form at least one element of an RF circuit component, and being selected to be affectable by a chemical and/or physical reaction with said at least one passive reactant, said chemical and/or physical reaction effecting a change in a signal generated by the RF circuit at a rate that is temperature dependent.

In yet another aspect, the present invention relates to a time-temperature indicator (TTI) device comprising at least one active reactant in the form of an electrically non-conductive layer forming at least one element of an RF circuit component, said at least one active reactant being selected to be affectable by a chemical and/or physical reaction effecting a change in a signal generated by the RF circuit at a rate that is temperature dependent.

In yet another aspect, the present invention relates to a time-temperature indicator (TTI) device comprising at least one active reactant in the form of an electrically non-conductive layer forming at least one element of an RF circuit component, said at least one active reactant being selected to be affectable by a chemical and/or physical reaction with at least one passive reactant, said chemical and/or physical reaction effecting a change in a signal generated by the RF circuit at a rate that is temperature dependent.

In yet another aspect, the present invention relates to a time-temperature indicator (TTI) device comprising at least one active reactant being a dielectric spacer of at least one capacitor, said at least one active reactant being selected to be affectable by a chemical and/or physical reaction with at least one passive reactant, said chemical and/or physical reaction effecting a change in an electrical property of said at least one capacitor.

In yet another aspect, the present invention relates to a time-temperature indicator (TTI) device comprising at least one active reactant being a dielectric spacer of at least one capacitor, said at least one active reactant being selected to be affectable by a chemical and/or physical reaction, said chemical and/or physical reaction effecting a change in an electrical property of said at least one capacitor.

In yet another aspect, the present invention relates to a time-temperature indicator (TTI) device comprising at least one active reactant being a part of at least one capacitor component, said at least one active reactant being selected to be affectable by a chemical and/or physical reaction with at least one passive reactant, said chemical and/or physical reaction effecting a change in an electrical property of said at least one capacitor.

In yet another aspect, the present invention relates to a time-temperature indicator (TTI) device comprising at least one active reactant being a part of at least one capacitor component, said at least one active reactant being selected to be affectable by a chemical and/or physical reaction effecting a change in an electrical property of said at least one capacitor.

In yet another aspect, the present invention relates to a time-temperature indicator (TTI) device comprising an active reactant in the form of an electrically conductive layer, said active reactant being selected to be affectable by a chemical and/or physical reaction effecting a change in reflectivity of said active reactant.

In yet another aspect, the present invention relates to a time-temperature indicator (TTI) device comprising an active reactant in the form of an electrically conductive layer, said active reactant being selected to be affectable by a chemical and/or physical reaction with at least one passive reactant, said chemical and/or physical reaction effecting a change in reflectivity of said active reactant.

In yet another aspect, the present invention relates to a time-temperature indicator (TTI) device comprising an active reactant in the form of a polymer layer transformable from its non electrically conductive state into an electrically conductive state, said active reactant being selected to be affectable by a chemical and/or physical reaction with at least one passive reactant, said chemical and/or physical reaction effecting said transformation of the active reactant into the electrically conductive material.

In yet another aspect, the present invention relates to a method of manufacturing a time-temperature indicator (TTI) device, the method comprising: selecting at least one material for at least one reactant to be a part of a component that is either an electrical component or transformable into an electrical component, said at least one reactant being selected so as to be affectable by a chemical and/or physical process effecting a change in an electrical property of said component; and incorporating said component into the TTI device.

Preferably, the method according to the present invention is characterized in that said process includes oxidation-reduction reaction.

Preferably, the method according to the present invention comprises selecting at least one passive reactant which, when exposed to temperature changes induced said chemical and/or physical reaction in said at least one active reactant. More preferably, the method according to the present invention comprises arranging the TTI device so as to expose the active reactant to the ambient, to thereby allow said chemical and/or physical reaction to be induced by the passive reactant from the ambient. More preferably, the method according to the present invention comprises incorporating said at least one passive reactant into the TTI device so as to provide a region of contact between the active and passive reactants. More preferably, the method according to the present invention is characterized in that said at least one passive reactant is a viscous substance selected to have a certain temperature such that the mobility and viscosity of said viscous substance change as a function of time when said viscous substance is exposed to a temperature higher than said certain temperature. More preferably, the method according to the present invention comprises selecting a viscous substance having a certain temperature such that the mobility and viscosity of said viscous substance change as a function of time when said viscous substance is exposed to a temperature higher than said certain temperature; and providing a region of contact between the active reactant and the viscous substance and exposing the viscous substance to the time and temperature environmental changes. More preferably, the method according to the present invention comprises attaching a label carrying the passive reactant to a structure including at least said active reactant. More preferably, the method according to the present invention comprises locating the passive reactant in a reservoir having an outlet and attaching said reservoir to a structure including at least the active reactant, thereby allowing passage of said passive reactant towards said structure. Even more preferred is a method that comprises providing a sealed enclosure on said reservoir, the enclosure being configured to allow at least partial removal thereof to thereby expose the passive reactant to the temperature changes.

Preferably, the method according to the present invention comprises enclosing said at least one active reactant in a sealed enclosure configured to be at least partly removed to thereby expose said at least one active reactant to the temperature changes.

Preferably, the method according to the present invention is characterized in that said electrical component is formed using at least one of the following: printing, CVD, PVD, sputtering, and patterning.

In yet another aspect, the present invention relates to a method of manufacturing a time-temperature indicator (TTI) device, the method comprising: selecting at least two material for at least two reactants such that at least one of these at least two reactants is an active reactant affectable by a chemical and/or physical reaction with at least one other passive reactant, wherein this chemical and/or physical reaction effects a change in an electrical property of a component with which said at least one active reactant is associated; and incorporating at least said component into the TTI device.

In yet another aspect, the present invention relates to a method of manufacturing a time-temperature indicator (TTI) device configured to provide a time-temperature dependent signal from an RF circuit, the method comprising: selecting an electrically conductive material from which at least one element of the RF circuit is to be configured, such that said electrically conductive material presents an active reactant affectable by a chemical and/or physical reaction effecting a change in the signal from the RF circuit.

Figure 1B:
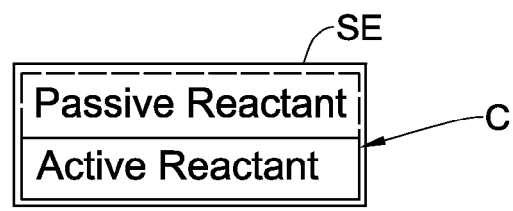
Figure 1C:
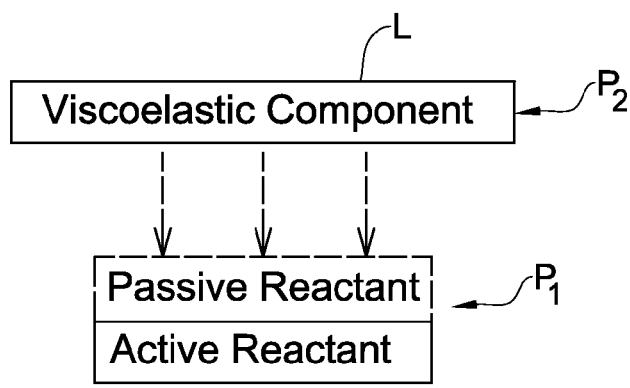
Figure 1D:
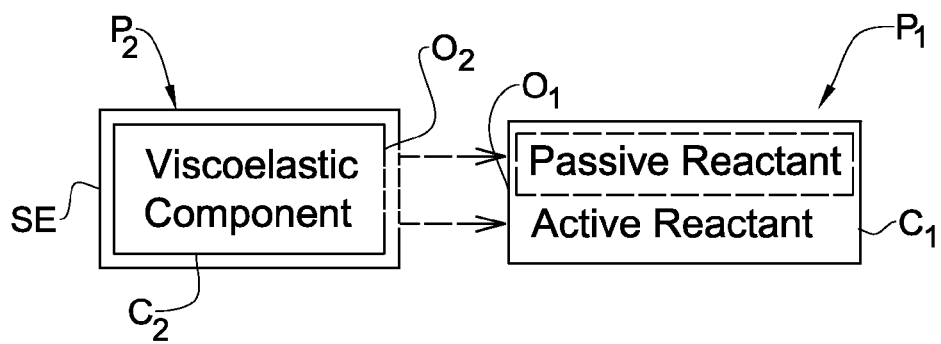
Figure 2A:
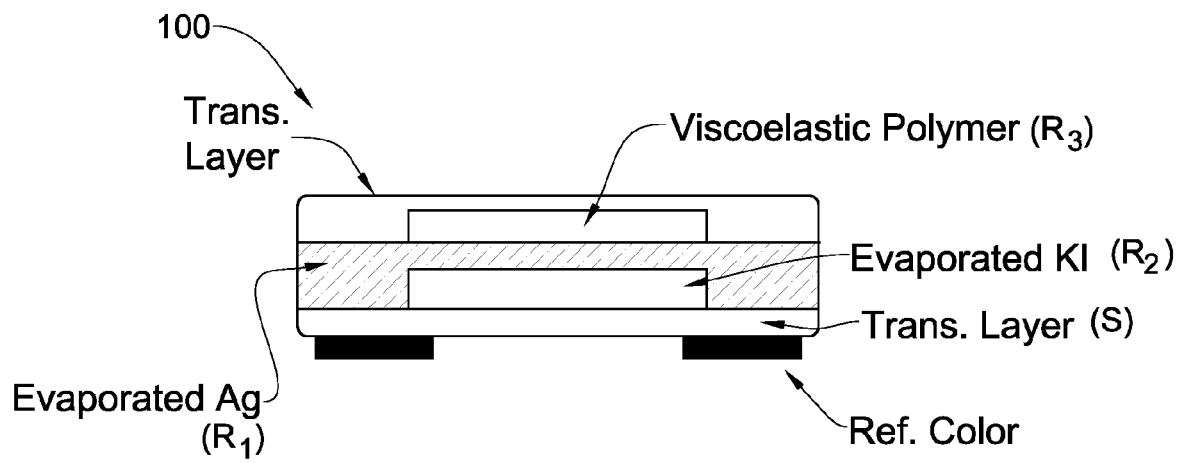
Figure 2B:
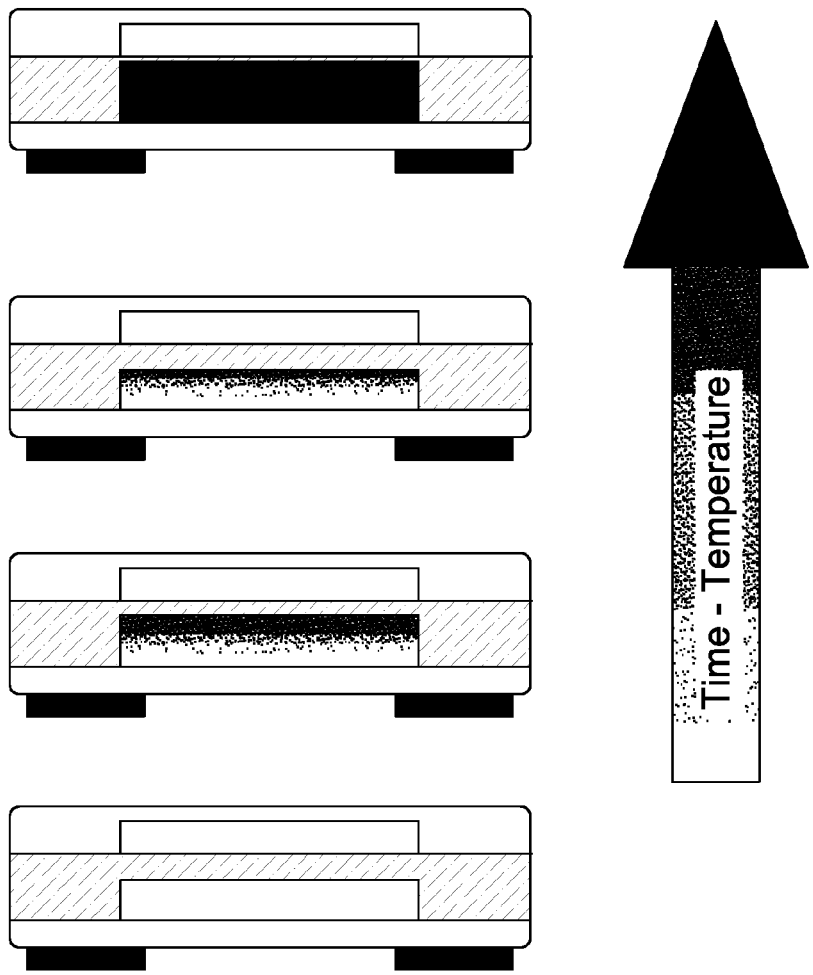
Figure 2C:
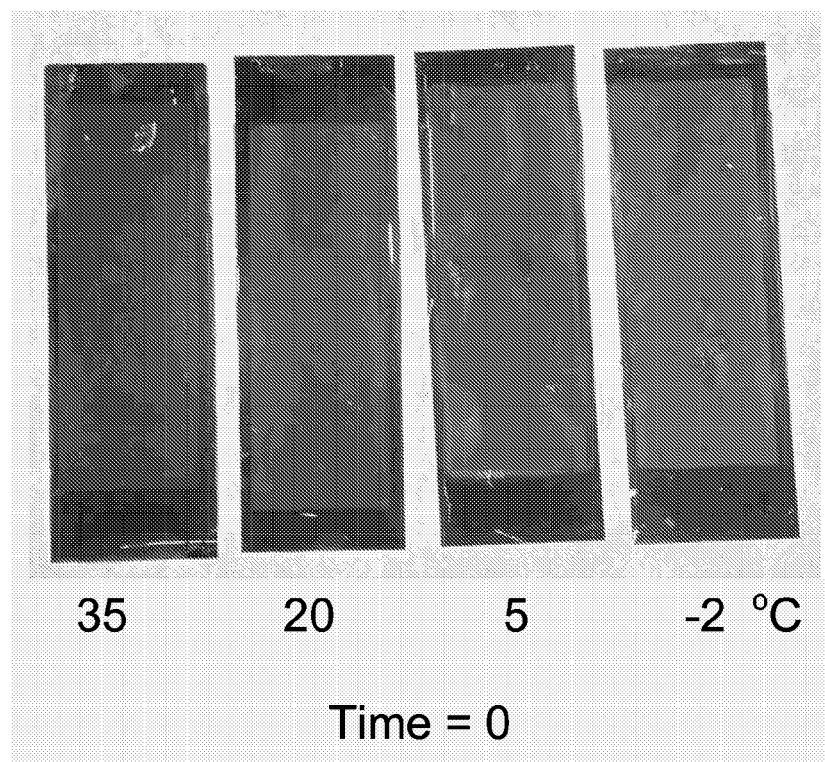
Figure 2D:
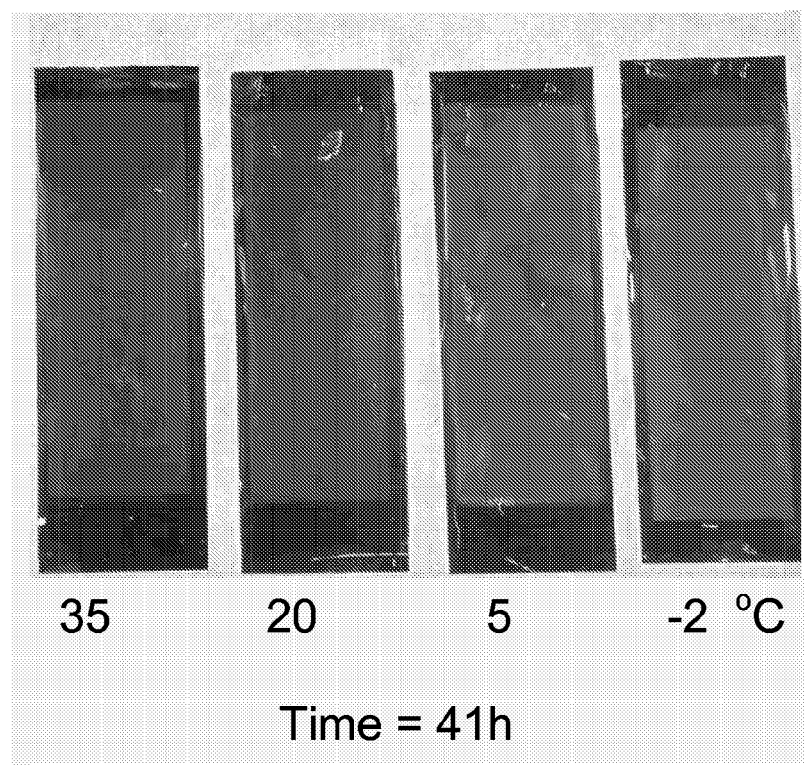
Figure 2F:
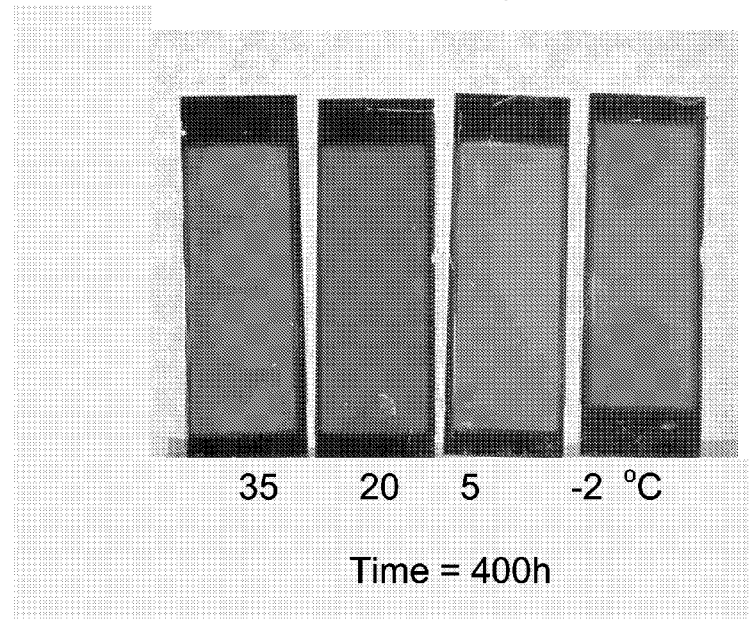
Figure 2E:
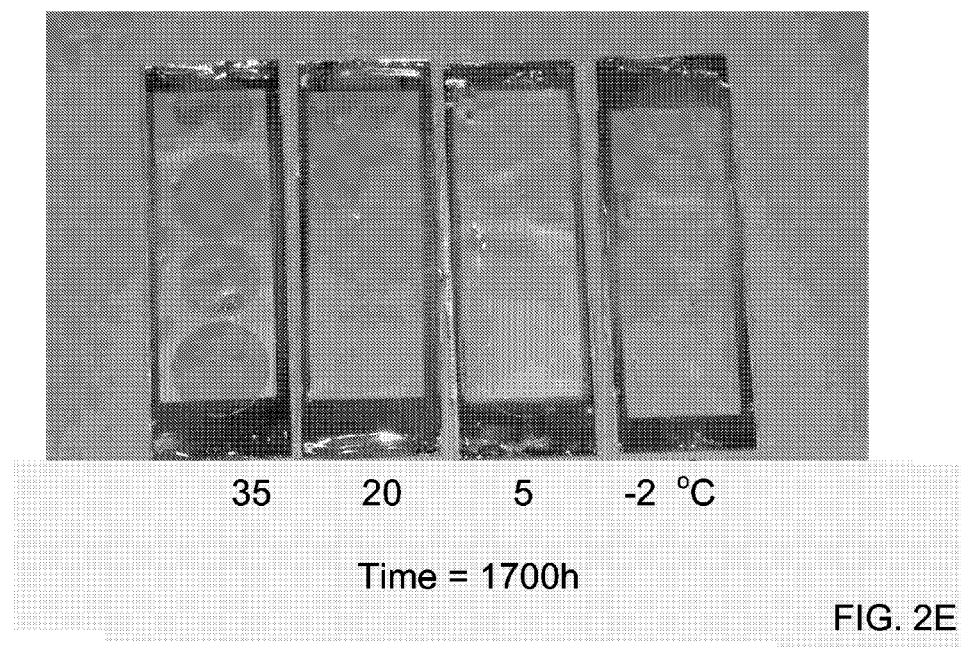

In order to better understand the invention and to see how it may be carried out in practice, further preferred embodiments will now be described by way of non-limiting examples and with reference to the accompanying drawings, in which:

FIG. 1A is a schematic illustration of a TTI structure according to one embodiment of the invention, utilizing passive and active reactants, with the active reactant being an electrically conductive material forming a resistor component or RF circuit;

FIGS. 1B to 1D schematically illustrate different examples of assembling and triggering a TTI device according to the present invention;

FIGS. 2A to 2H illustrate experimental results of the technique of the present invention showing the time-temperature dependent changes in the reflectivity and resistivity of an electrically conductive active reactant, where FIG. 2A shows an experimental TTI structure 100, FIG. 2B shows the time-temperature development of a mixing process between the active and passive reactants, FIGS. 2C-2H show the time and temperature dependent changes in the active reactant.

Figure 3:
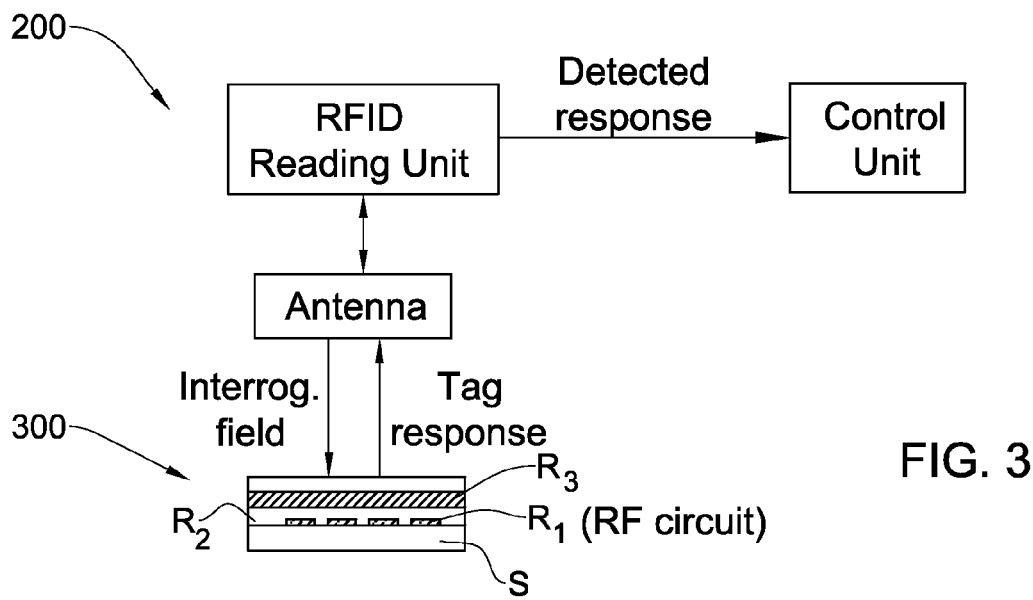
Figure 5:
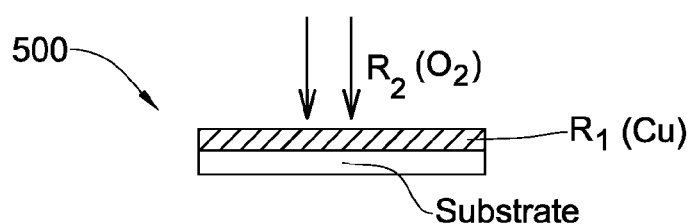
Figure 6:
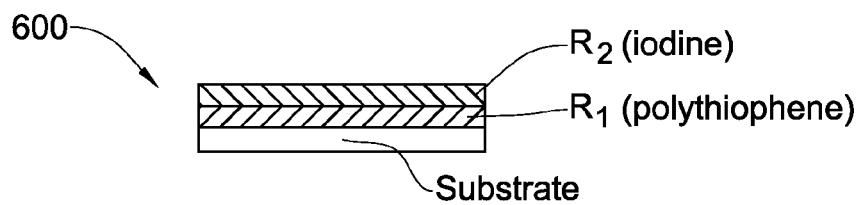

FIG. 3 schematically illustrates a system for reading a TTI device of the present invention utilizing an active reactant in the form of an RF circuit;

FIGS. 4A-4C, 4D and 4E exemplify different configurations, respectively, of a TTI structure utilizing an active reactant as a part of a capacitor component;

FIG. 5 is a schematic illustration of yet another example of a TTI structure utilizing an active reactant in the form of an electrically conductive layer affectable by the ambient; and FIG. 6 is a schematic illustration of a TTI structure according to yet another embodiment of the invention utilizing an active reactant in the form of a material transformable into an electrically conductive material.

Referring to FIG. 1A, there is schematically illustrated a TTI structure of the present invention, generally designated 10. Generally, the TTI structure includes an active reactant of the kind that is capable of inducing or undergoing a physical and/or chemical reaction affecting the electrical property of the active reactant or an electric component with which the active reactant is associated. The active reactant may be an electrically conductive material (metal or semiconductor) that reduces its conductivity at a rate that is temperature dependent; or may be a non-conductor that increases its conductivity at a rate that is temperature dependent. In the present example of FIG. 1A, the TTI structure 10 includes a first, active reactant $R_1$ and a second, passive reactant $R_2$, which in the present example are located adjacent to one another to be in contact. The active reactant $R_1$ is initially an electrically conductive layer (e.g., silver) presenting a resistor component. The active reactant $R_1$ is located on an electrically insulating substrate S. It should be noted that such an initially electrically conductive active reactant may be configured as an RF circuit component or one of the RF circuit's features (e.g., antenna); or may be the electrode of a capacitor component in which case the passive reactant $R_2$ may be a dielectric spacer of the capacitor. The passive reactant $R_2$ disintegrates the electrically conductive material of the active reactant (affects the homogeneity thereof) at a rate proportional to the time and temperature changes developing in the passive reactant $R_2$, thus affecting the electrical property (resistance) of the active reactant.

The TTI structure 10 preferably also includes a viscous material (termed herein "viscoelastic component) $R_3$ serving as a second passive reactant. The viscoelastic component is selected to exhibit a change in viscosity, or a phase transfer (from solid to liquid), that is dependent upon the temperature of the surroundings to which the viscoelastic component is exposed.

The TTI structure is preferably appropriately sealed such as to avoid interaction between the passive and active components and water from the surroundings.

The substrate S is a substantially transparent layer, such as glass, polymer film, etc., preferably formed with an adhesive coating on its outer surface to allow attachment of the TTI to a specific item.

The passive reactant $R_2$ may be a salt layer (such as KI, KCl, NaCl, KOH, NaOH, carbonate salts etc.). The viscoelastic layer $R_3$ may for example be a polymer, e.g., polymer having an ionic character, such as polystyrenesulfonate derivatives.

The electrically conductive layer $R_1$ may be deposited on the substrate S using evaporation and/or electroless deposition and/or electrical means, etc. The passive reactant $R_2$ layer may for example be deposited atop the first reactant containing layer by evaporation (any other means may be used as well).

A viscoelastic material is one which exhibits elastic and viscous properties simultaneously. Viscoelastic materials are sometimes classified as either viscoelastic solids, i.e., elastic solids which exhibit some viscous effects during deformation, or viscoelastic liquids, i.e., viscous liquids which exhibit some elastic effects. A viscoelastic liquid can be identified as a viscoelastic material which continues to deform indefinitely when subjected to a shearing stress. A viscoelastic material may exhibit a transition from an immobile, glassy state to a viscoelastic liquid state at a temperature known as the glass transition temperature. It may also exhibit a transition from a partially crystalline state to an amorphous state at the temperature at which the crystalline material melts.

A viscoelastic material may also be chemically crosslinked, rendering it a viscoelastic solid. It may also be physically crosslinked by the presence of crystalline or glassy dispersed phases which are chemically coupled to the matrix phase. It may also exhibit viscoelastic solid properties because of the presence of ionic bonding or hydrogen bonding between polymer molecules (John D. Ferry, Viscoelastic Properties of Polymers, John Wiley & Sons, Inc. 1980.

The viscoelastic material used with the device of the present invention may be a liquid or a solid material. A viscoelastic liquid state is one which remains liquid at all temperatures to which the object to be monitored will be exposed. Such a viscoelastic material has all such thermal transitions at temperatures below the anticipated range of temperatures to which the object to be monitored will be exposed. This allows for an indicator which will be in its activated state upon contacting the viscoelastic material with the porous matrix. This also allows the viscoelastic material to migrate into the matrix throughout the entire anticipated temperature range. In this manner, the indicator will be able to provide continuous integration of time-temperature exposure over the entire range of temperatures to which the object to be monitored is exposed.

Solid viscoelastic materials are those which function when the modulus of the material is low enough for it to deform and penetrate entirely through the porous matrix under the influence of capillary action or other driving forces present in the device.

Non-limiting examples of viscoelastic materials which may be suitable for use with the indicator of the present invention include natural rubber, butyl rubber, polybutadiene and its copolymers with acrylonitrile and styrene, poly alpha olefins such as polyhexene, polyoctene, and copolymers of these and others, polyacrylates, polychloroprene, silicone pressure sensitive adhesives, and block copolymers such as styrene-isoprene block copolymers, and mixtures of any of the above.

The viscoelastic component may or may not have a solid-to-liquid transition at temperatures that are relevant to the specific application, and consequently the use of the appropriately selected viscoelastic component allows for monitoring either partial or full time-temperature history of the TTI. The viscoelastic component is selected to be characterized by that when being exposed to temperatures higher than a certain threshold temperature specific for said viscoelastic component, it undergoes a change in its mobility and ability to dissolve and transport other chemical substances and propagate in porous solids. Such a change may cause a phase change process in the other passive reactant $R_2$ thereby causing time dependent development of the chemical and/or physical reaction between the active reactant $R_1$ and the passive reactant $R_2$.

Thus, the viscoelastic component (e.g., polymer) $R_3$, used with the device of the present application, is selected to be characterized by a certain temperature $T_g$, such that at a temperature $T_1$ below this temperature $T_g$, the polymer is characterized by a substantially low mobility and substantially high viscosity, and at a temperature $T_2$ higher than $T_g$ the mobility is relatively high and viscosity relatively low. The viscosity of the polymer varies with temperature as it is exposed to temperatures higher than $T_g$. When the viscosity of the polymer layer reduces, it causes dissolution of the salt layer $R_2$ in the polymer $R_3$, thus causing the dissolved salt to slowly penetrate towards the electrically conductive reactant $R_1$ and act to replace parts of the electrically conductive material or to react therewith thereby disintegrating the electrically-conductive material.

Thus, at temperatures $T_1$, little or practically no reaction between the passive and active reactant layer materials $R_2$ and $R_1$ occurs, and the status of the TTI 10 is practically time independent. At temperatures $T_2$ that are higher than the $T_g$, the reaction occurs at a rate that is proportional to the time-temperature conditions history, and the status of the TTI 10 (at least its electrical property) is time dependent. At these temperatures, the electrically conductive layer $R_1$ (e.g., silver) disintegrates and its electrical property (conductivity), as well as the optical property (reflectivity), varies as the function of the aggregated time-temperature history. It should be understood that depending on whether partial or full time-temperature indication is needed, the viscoelastic component is appropriately chosen to have its threshold temperature $T_g$, respectively, within the temperature range of interest for a specific application, or outside the temperature range (taking into account whether an increase or decrease of temperature is expected when the device is exposed to the temperature changes).

It should be noted that the provision of two passive reactants is optional, and the single passive reactant $R_2$ may be directly exposed to the environmental changes. A viscous substance, when used, may actually serve as the single passive reactant (thus eliminating the need for the other reactant $R_2$ in FIG. 1A), such that a time and temperature change in the viscoelasticity thereof effects a change in the detectable electrical properties of the active reactant $R_1$ or the component with which the active reactant is associated, e.g., RF circuit as will be exemplified further below.

The reaction between the passive and active reactant materials may be physical and/or chemical in nature. Physical reactions may for example be, but are not limited to, such reactions in which a result is a replacement, disintegration, dissolution, dislocation, segregation, mixing or insertion of the passive reactant, usually a soluble salt, into the substructure of the active reactant, typically the material making the conductive layer. In other embodiments of the invention, the meaning of physical processes/reactions may be the process of wetting and progression of a liquid material into a porous/absorbing static material or the mixing of two liquids, etc. Chemical reactions may for example be acid-base reactions, oxidation-reduction reactions, salt forming reactions, and other reactions which may or may not be reversible in nature.

Generally, the active reactant material(s) may be any reactant(s) capable of inducing or undergoing physical or chemical reaction affecting an electrical property of the active reactant. The active and passive reactants may for example be, respectively, a metal and an oxidizing agent; a metal oxide and a reducing agent; a metal or semiconductor and a disintegrating agent such as KI, HCl, KOH, NaOH, and the like; metal salt and an agent such as oxidizer, reducer, or disintegrating agent. Examples of metals and metal oxides suitable to be used in the active reactant include but are not limited to silver, gold, aluminum, copper, nickel, etc. and oxides or salts thereof. It should be understood that in the embodiment of the present invention where the active reactant includes an electrically conductive material, the only requirements to this electrically conductive active-reactant material are: capability of being oxidized or reduced, or disintegrated by a selective material for the passive reactant, which may and may not be a physical component of the TTI (as will be described further below).

According to some other embodiments of the invention, the active reactant is a dielectric material, as will be described further below.

It should also be noted that the term "disintegration" used herein refers to a change in the homogeneity of the material, which may be caused by one of the following effects: oxidation, reduction, material removal (e.g., dissolution).

Turning back to the example of FIG. 1A, the reaction between the active and passive reactant materials results in affecting the homogeneity of the electrically-conductive layer material $R_1$, and consequently affects the electrical characteristics of this material, especially the electrical resistance changes dramatically, and also affects the light response of this layer, i.e., the reflectivity of the layer reduces. Since the reaction is expressed in the dissolution of the metal layer, the electrical resistance changes from values that are typical for conductors to values that exhibit insulating materials.

Reference is made to FIGS. 1B to 1D exemplifying the assembling and triggering of a TTI device according to the invention.

In the example of FIG. 1B, a TTI structure is formed by an active reactant (or an electrical component including an active reactant as one of its elements) and possibly also a passive reactant (shown in the figure in dashed lines as its provision is optional), and is located in a container C, which is initially placed in a sealed enclosure SE. Considering the TTI structure formed only by active reactant, the reactant is an electrically conductive material. The sealed enclosure is configured such as to allow breaking or removing or puncturing the enclosure SE to thereby put the TTI device in operation, i.e., expose the TTI structure to the environmental changes. It should be understood that if the TTI structure includes active and passive reactants, the passive reactant may be liquid with the active reactant being embedded therein.

In the example of FIG. 1C, a TTI structure is a two-part structure: one part $P_1$ is by itself inactive and in order to put the TTI device in operation is to be assembled with the other part P$_2$. The "inactive" part P$_1$ includes an active reactant (or an electrical component including an active reactant as one of its elements) and possible also a first passive reactant (shown in the figure in dashed lines as its provision is optional). The other part P$_2$ includes a viscoelastic polymer or liquid serving as passive reactant. The viscoelastic polymer or liquid is associated with a separate label L, namely is either placed on a sticky label or a sticky viscoelastic polymer is selected (as mentioned above). Applying the sticker L atop the inactive TTI outs the TTI device in operation.

FIG. 1D exemplifies a TTI structure configured as a two-part device, including an initially inactive part P$_1$ having an active reactant (or an electrical component including an active reactant as one of its elements) and possibly also a first passive reactant (shown in the figure in dashed lines as its provision is optional) located in a container C$_1$ having an inlet opening O$_1$; and the other part P$_2$ including a viscoelastic component, which is initially solid and is located in a container C$_2$ having an outlet opening O$_2$ and a sealed enclosure SE. The latter is configured to allow breaking, removing or puncturing thereof and to be attachable to the inactive-part container so as to define a liquid passage between the two containers via inlet and outlet openings.

FIGS. 2A to 2H illustrate experimental results of the technique of the present invention showing the time-temperature dependent changes in the reflectivity of an electrically conductive active reactant. FIG. 2A shows an experimental TTI structure 100 formed by a transparent electrically insulating substrate layer S such as glass; a first passive reactant layer R$_2$, which is typically a 100 nm KI that is evaporated atop the substrate layer S; an active reactant layer R$_1$ which is typically a 100 nm silver mirror layer that covers the entire layer of KI also from the sides to avoid contact between KI and humidity; and a second passive reactant layer R$_3$ which is a viscoelastic polymer. The structure 100 also includes an uppermost transparent layer.

Figures 2G, 2H:
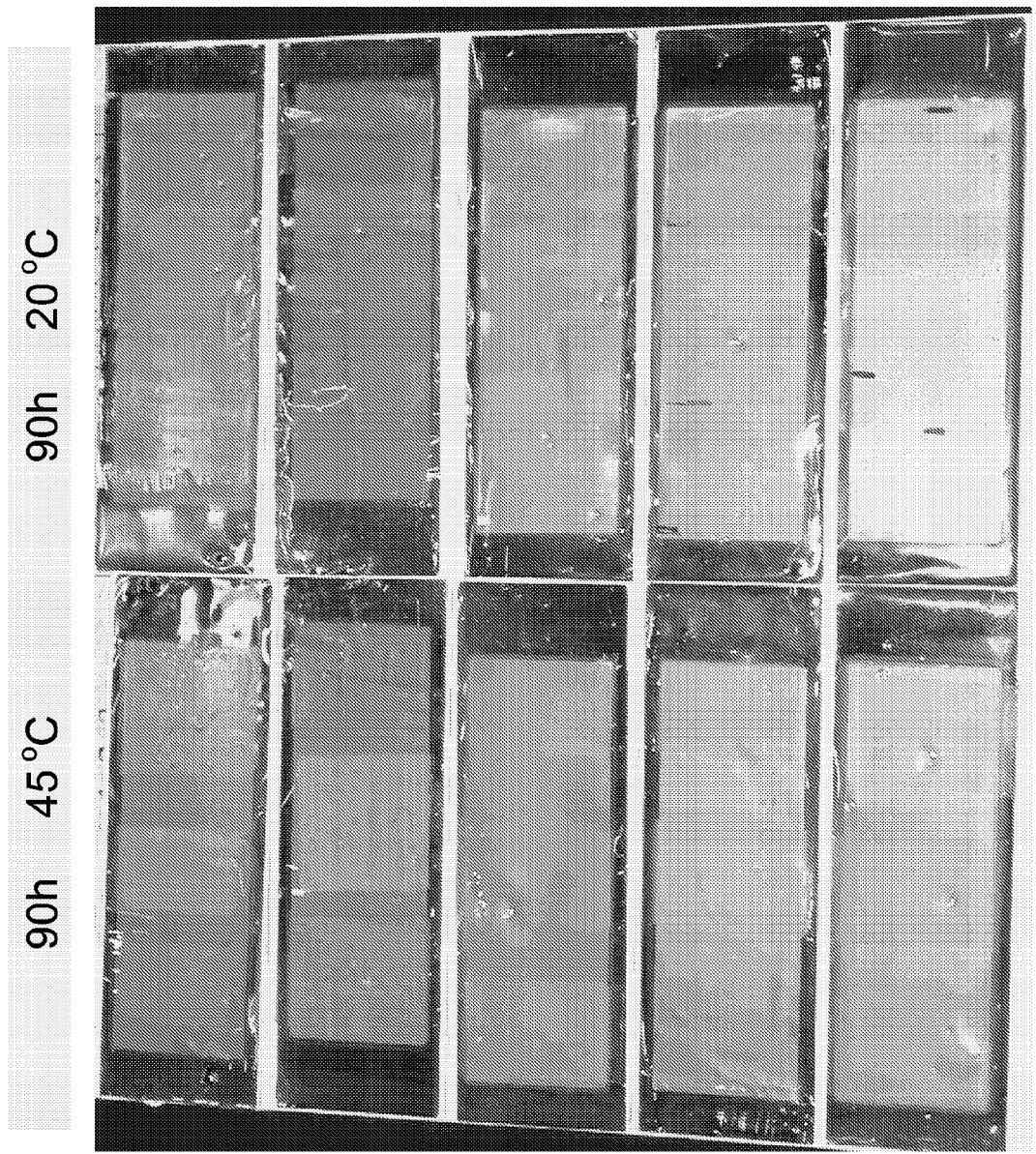

The viscoelastic polymer R$_3$ mixes the materials of layers R$_1$ and R$_2$ at a rate that is a function of the temperature. FIG. 2B shows the time-temperature development of such a mixing process. FIGS. 2C-2F show the temperature dependent changes on the active reactant layer R$_1$ (temperature varies from 35° C. to (−2)° C. for respectively, the following time points: the starting point (time=0), and 41, 400, and 1700 hours thereafter. FIGS. 2G and 2H show the results of the active reactant changes after 90 hours of the reaction development for, respectively, 450 and 20° C. of the environmental conditions and different viscoelastic mediators.

The inventors have conducted experiments with different viscoelastic polymers. The results were different time temperature profiles. The reflectivity of the electrically conductive active reactant decreases in response to rising temperatures and time.

It should be understood that by replacing the glass substrate S in the structure 100 by a polymer coated ITO, a capacitor arrangement is formed by two electrodes (layer R$_1$ and polymer coated ITO substrate S) and a dielectric spacer between them formed by the KI layer R$_2$. In this case, mixing of layer materials R$_1$ and R$_2$ would affect the capacitance of this structure in a manner which can easily be detectable.

Referring to FIGS. 1 and 2A, it should also be understood that the electrically conductive active reactant layer R$_1$ may be patterned to form an RF circuit to thereby operate as an RF tag. The construction and operation of RF tags are known per se and therefore need not be described in details, except to note the following. Generally, RF tags can be active (i.e., utilizing an internal energy source incorporated with the tag) or passive that function using the energy of an external interrogation signal. RF tags are dependant on energy supplied from a tag reader or an external device. RF tag includes an antenna attached to a resonance or oscillatory circuit (typically including capacitive, inductive and resistive elements), which is energized (e.g., by the received interrogation signal) and which, when energized, excites the antenna to transmit an RF response signal at a resonance frequency of the circuit. Antennas used in an RF ID tag are generally constituted by loops of wire or metal etched or plated on the tag surface.

FIG. 3 schematically illustrates a system 200 for reading a TTI device 300 of the present invention. In the present example, the device 300 includes a TTI structure similar to that of FIG. 1, but it should be understood that the structure configuration of FIG. 2A can also be used, as well as a structure having a single passive reactant.

The RF tag pattern may have various code or memory configurations. The most simple is the single code tag (such as typically utilized in EAS systems). Such a tag emits a single response when activated by a reader. The response is a simple "YES" or "NO", indicating whether or not the tag is present or activated. Alternatively, the RF tag pattern may define a plurality of resonant circuits, each for outputting a response signal at a predetermined frequency in response to an interrogating signal. The response signals define a response code of the entire tag, which is determined by the number of individual circuits and the manner of their operation. RF configurations suitable to be used in the present invention are disclosed for example in U.S. Pat. Nos. 6,104,311 and 6,304,169. Thus, generally, the RF tag includes at least one resonance circuit. The elements of the RF tag can be printed on the substrate layer (in a known manner by using conductive inks), or the continuous electrically conductive layer is deposited on the substrate and then patterned to define the elements of the tag. The magnitudes of the capacitive, inductive and resistive elements can be predefined as a part of the printing/patterning process, in accordance with a frequency representing a code element of the RF tag.

The system 200 includes an interrogating antenna 202A, an RF ID reader 204 and a control unit 206. While the TTI device 300 (a product with which the TTI is associated) is exposed to the time-temperature environmental changes, a reaction between the active and passive reactants develops, thus effecting a change in the electrical property of at least one RF tag feature and accordingly effecting a change in the RF tag response to the interrogating field. To detect this change, the antenna 202 energizes (interrogates) the TTI by a reading field and the TTI response is detected by the reader 204, which generated data indicative of the detected response and transmits this data to the control unit 206. The principles of the RF tag reading are known per se and therefore need not be described in details.

Figure 4A:
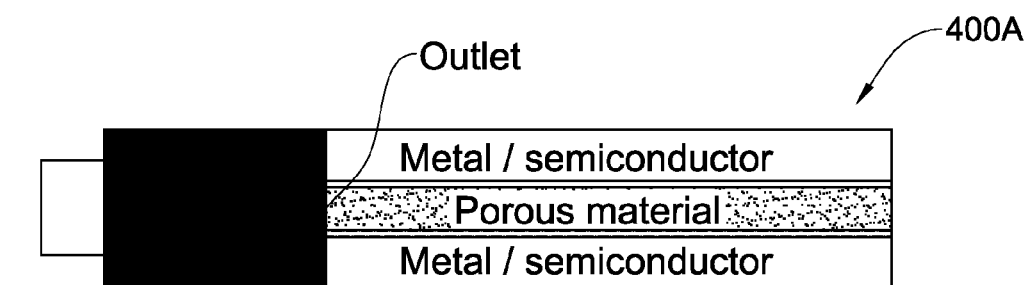
Figure 4B:
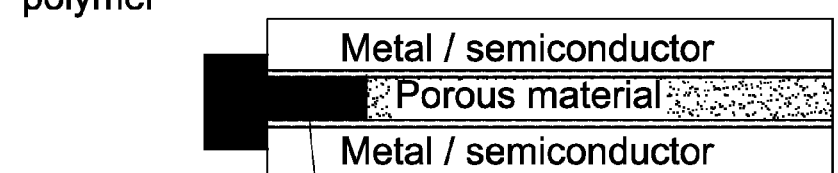
Figure 4C:
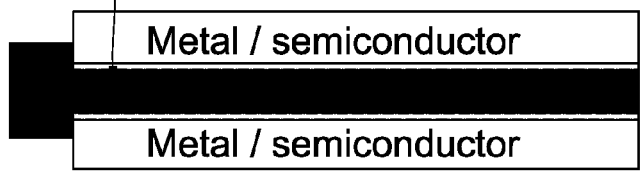

Reference is made to FIGS. 4A to 4E illustrating yet another examples of a TTI structure of the present invention including an electrical component configured as a capacitor. In the example of FIGS. 4A-4C, a TTI structure 400A includes a capacitor component formed by two electrodes E$_1$ and E$_2$ and a dielectric spacer between them in the form of a porous material; and a reservoir containing a viscoelastic polymer or any other viscous material. The reservoir is located adjacent to the capacitor component and has an outlet allowing the viscoelastic polymer passage to the capacitor component. FIG. 4A shows the starting point, or inoperative position of the TTI device (for example, the reservoir may have a sealed enclosure to be broken, removed or punctured to put the device in operation). FIG. 4B shows the device after some time, during which the viscoelastic component penetrates into the porous material, thus causing a change in the capacitance, indicating the time-temperature history of the device. FIG. 4C shows the device after some more time: the viscoelastic component completely fills the porous material, the capacitance changes and indicates longer time-temperature history. It should be noted that the electrode(s) may be transparent for the provision of simple visual time-temperature progression as well, by measuring a distance the viscous liquid penetrated the porous material.

The viscoelastic component penetration into the dielectric spacer affects the dielectric permeability of the spacer material thus affecting the capacitance, in which case a dielectric spacer of the capacitor presents an active reactant, namely has a time-temperature varying dielectric permeability thereby effecting a change in the electrical properties of the capacitor component. Additionally, the dielectric spacer material may be selected similar to the above-described example of FIG. 1A such that, while being dissolved in the viscoelastic component it affects the homogeneity of the electrode layer, which presents an active reactant.

Figure 4D:
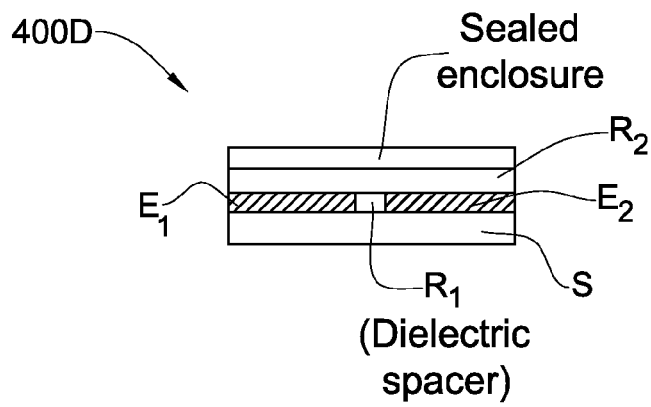
Figure 4E:
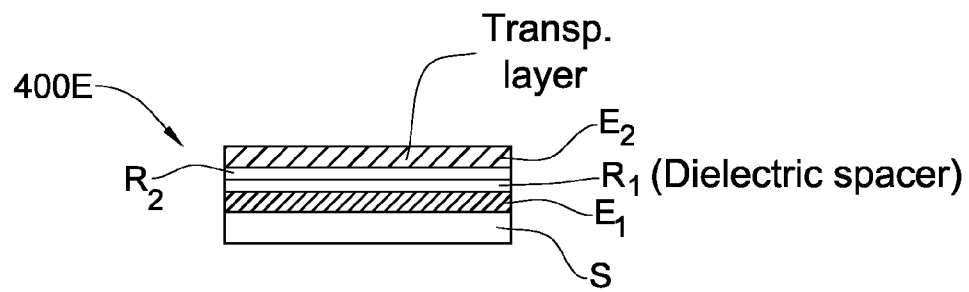

In the example of FIG. 4D, a TTI structure 400D includes an electrically insulating substrate layer S (e.g., glass); an electrically conductive layer on top of the substrate patterned to define electrodes $E_1$ and $E_2$; a dielectric spacer layer D between the electrodes presenting an active reactant $R_1$, which is a porous and insulating layer such as even a paper layer or a porous metal oxide layer; a viscoelastic layer $R_2$; and a removable enclosure. As the viscoelasticity of layer $R_2$ changes with time and temperature (as described above), this viscoelastic liquid penetrates the layer $R_2$ and creates time-temperature changes in the capacitance, as a result of a change in the dielectric permeability of the spacer layer $R_1$. In the example of FIG. 4E, a TTI structure 400E includes an insulating substrate S coated with an electrically conductive layer presenting a first electrode $E_1$; a porous and insulating layer such as even a paper layer to be a dielectric spacer of a capacitor and presenting an active reactant $R_1$; a viscoelastic layer (passive reactant $R_2$); and a second electrode $E_2$ layer (which may or may not be transparent) on top of the viscoelastic layer $R_2$. The viscoelastic layer $R_2$ is exposed to the time and temperature changes of the environment via the electrode $E_2$ and/or via regions of layer $R_2$ outside the electrode $E_2$.

It should be understood that two additional insulating layers may be used in the structures 400A and 400B that insulate the conductive layers from any ionic conductance that may occur if the viscoelastic layer is an ionic or charge conductor.

It should also be noted that the capacitor component of FIGS. 4A-4E may be an element of an RF circuit, in which case the time-temperature changes in the dielectric spacer $R_1$ of the capacitor effect a change in the RF signal from the RF circuit.

Starting from a RF circuit with a first normal capacitor (C1), a resistor (R1), an antenna (L1) and a second time temperature responsive capacitor, the capacitance of C2 varies with time at a rate that is temperature dependent. It may be that the temperature dependency is continuous or it has a threshold so that below a given temperature the evolution of the capacitance in time is negligible.

Assuming that R1 is a constant resistor, the resonance frequency is $$2\pi f_{Not\ spoiled} = \sqrt{\frac{1}{L(C1+C2)}}$$

at time=0 from activation. When the capacitance of C2 drops to zero or to any pre defined value C2', the frequency reaches the frequency that defines a spoiled good $$\left(2\pi f_{Spoild} = \sqrt{\frac{1}{L(C1+C2')}}\right).$$

Capacitance change is the only factor, which needs to be considered. To this end, a capacitor is used with the following architecture:
Viscous layer with de-doping agent
Metal grid
Doped conjugated polymer
Insulating layer
Metallic electrode Upon placing the viscous layer that contains the de-doping agent atop the metal grid that is positioned on top of the doped conjugated polymer, said viscous layer that contains the de-doping agent causes the de-doping of said doped conjugated polymer at a rate that is time temperature dependent, thus changing the capacitance of C2 and the resonance frequency of said circuit.

Other electric and/or electronic properties of the device such as the resistance of the doped conjugated layer when it acts as the resistor R1, its AC and DC response may be changed at a rate that is temperature dependent. In the case of the resistance of R1, the effect is mainly expressed in the Q factor of the resonating circuit.

It should be clear that the term a rate that is time temperature dependent may mean that the outcome is a gradual change in the electronic properties but in other embodiments, it may result in a sudden change in the electronic properties.

Yet another example of inducing time-temperature changes in electrical properties of the TTI via the dielectric spacer of a capacitor is by using a series of capacitors, rather a single capacitor, that break when a viscoelastic polymer penetrates to them, in which case the time-temperature profile is measured by the number of capacitors that have been affected (i.e., penetrated by the viscoelastic component). It should be understood that the same viscoelastic polymer may be used for penetrating the capacitors one after the other; different viscoelastic polymers, having different penetration rates, may be used; different porous materials within the capacitors may be used; and/or different spacings in between the electrodes of the capacitors may be used.

The device of the present invention may be manufactured using any known suitable techniques, including for example ink jet printing, offset printing, gravure, etc.

Reference is made to FIG. 5, showing yet another embodiment of the invention. Here, a TTI structure 500 is configured to utilize, as its constructional element, only an active reactant $R_1$ in the form of an electrically conductive layer of a kind undergoing oxidation when exposed to the ambient. This may be Cu, GaAs, etc. A passive reactant $R_2$ (oxygen) comes from the environment. The time-temperature dependent oxidation will thus result in a change of conductivity of the layer $R_1$ as well as the reflectance thereof. Here again, if the layer $R_1$ is patterned to form an RF circuit, the oxidation of this layer will effect a change in the circuit response to an interrogation field.

FIG. 6 illustrates yet another example of the invention. A TTI structure 600 is shown including an active reactant layer $R_1$ (on top of a substrate) which is a polymer layer of the kind that is initially non-conductive and is transformable into an electrically conductive material; and a passive reactant $R_2$ selected to affect the electrical conductivity of the active reactant $R_1$ so as to transfer it into an electrically conductive material. The active reactant $R_1$ may be polythiophene, and the passive reactant $R_2$ may be iodine ($I_2$) or a complex of iodine (say iodine complexed to starch) or iodine that is dissolved in a polymeric matrix. When exposed to the ambient, iodine $R_2$ slowly sublimes and penetrates through the polythiophene layer $R_1$. This induces electrical conductivity to the polythiophene layer $R_1$. In this case, the TTI state change can be detected by measuring an electric current through the active reactant layer $R_1$, and can also be detected visually since the polythiophene while becoming a conductor changes its color to black.

The invention claimed is:

1. A time-temperature indicator device comprising
   (i) at least one active reactant being at least a part of an electrical component, said at least one active reactant is selected such that it changes at least an electrical property of said at least a part of said electrical component at a rate that is temperature dependent or time-temperature dependent, wherein the active reactant is a metal or an oxide thereof, or a semiconductor, and
   (ii) at least a first passive reactant in the form of a viscous substance; wherein said viscous substance is in contact with said active reactant, such that said at least one active reactant reacts with said at least a first passive reactant to induce temperature dependent or time-temperature dependent disintegration of said active reactant, wherein said at least a first passive reactant and said active reactant are selected such that they cause temperature dependent or time-temperature dependent development of said temperature dependent or time-temperature dependent disintegration, thereby effecting a change in at least an electrical property of said at least a part of an electrical component at a rate that is temperature dependent or time-temperature dependent;
   wherein said change in at least an electrical property of said at least a part of an electrical component is associated with a change in a visual physical property of the indicator device.

2. A time-temperature indicator device comprising (i) at least one active reactant being at least a part of an electrical component, wherein said electrical component comprises an electrically conductive material, said at least one active reactant is selected such that it intrinsically changes at least an electrical property of said at least a part of said electrical component at a rate that is temperature dependent, said at least one active reactant is selected such that it intrinsically changes at least an electrical property of said at least a part of said electrical component at a rate that is temperature dependent, wherein the active reactant is a metal or an oxide thereof, or a semiconductor; (ii) at least one first passive reactant in the form of a viscous substance; and (iii) at least one second passive reactant, wherein said at least one first passive reactant is located between said at least one active reactant and said at least one second passive reactant, wherein said at least one second passive reactant is a viscous substance wherein said chemical and/or physical reaction is a reaction between said at least one active reactant and said at least one second passive reactant and wherein said at least one first passive reactant is selected such that it causes time dependent transfer of heat towards said at least one second passive reactant thereby causing time-temperature dependent development of said chemical and/or physical reaction.

3. The time-temperature indicator device according to claim 1, wherein said electrical component is selected from the group consisting of resistor, capacitor, diode, inductance coil and antenna.

4. The time-temperature indicator device according to claim 1, wherein said chemical and/or physical reaction is selected from the group consisting of acid-base reaction, oxidation-reduction reaction and salt forming reaction.

5. The time-temperature indicator device according to claim 1, wherein said chemical and/or physical reaction consists of mixing said at least one active reactant and said at least one first passive reactant, thereby causing a change in permeability of the at least one active reactant.

6. The time-temperature indicator device according to claim 1, configured as a two-part device, wherein one of the two parts includes at least the at least one active reactant, and the other part includes the at least one first and/or second passive reactant, the two parts being configured to be attachable to one another to thereby induce said chemical and/or physical process and thereby put the device in operation.

7. A method of time temperature indication comprising performing a chemical and/or physical reaction between at least one active reactant and at least one passive reactant effecting a change in at least an electrical property of an electrical component wherein said at least one active reactant is at least a part of an electrical component, wherein said electrical component comprises an electrically conductive material, wherein the active reactant is a metal or an oxide thereof, or a semiconductor, and wherein said at least one passive reactant is a viscous substance; wherein said viscous substance is in contact with said active reactant, such that said performing said chemical and/or physical reaction comprising reacting said at least one active reactant with said at least one passive reactant to induce temperature dependent or time-temperature dependent disintegration of said active reactant, wherein said at least one passive reactant and said active reactant are selected such that they cause temperature dependent or time-temperature dependent development of said temperature dependent or time-temperature dependent disintegration, thereby effecting a change in at least an electrical property of said at least a part of an electrical component at a rate that is temperature dependent or time-temperature dependent; wherein said change in at least an electrical property of said at least a part of an electrical component is associated with a change in a visual physical property of the indicator device.

8. A packaging material or a label, comprising the time-temperature indicator device according to claim 1.

9. The time-temperature indicator device according to claim 2, wherein said chemical and/or physical reaction is selected from the group consisting of acid-base reaction, oxidation-reduction reaction and salt forming reaction.

10. The time-temperature indicator device according to claim 2, wherein said chemical and/or physical reaction consists of mixing said at least one active reactant and said at least one first passive reactant, thereby causing a change in permeability of the at least one active reactant.

11. The time-temperature indicator device according to claim 2, configured as a two-part device, wherein one of the two parts includes at least the at least one active reactant, and the other part includes the at least one first and/or second passive reactant, the two parts being configured to be attachable to one another to thereby induce said chemical and/or physical process and thereby put the device in operation.

12. The time-temperature indicator device according to claim 1, wherein said at least one active reactant is a metal selected from the group consisting of silver, gold, aluminum, copper and nickel, or an oxide thereof.

* * * * *

UNITED STATES PATENT AND TRADEMARK OFFICE
CERTIFICATE OF CORRECTION

| | | |
|---|---|---|
| PATENT NO. | : 8,267,576 B2 | Page 1 of 1 |
| APPLICATION NO. | : 11/666886 | |
| DATED | : September 18, 2012 | |
| INVENTOR(S) | : Dietrich Haarer et al. | |

It is certified that error appears in the above-identified patent and that said Letters Patent is hereby corrected as shown below:

On the Title page, add a section entitled --Related U.S. Application Data-- followed by the benefit data as follows:

--(60)   Provisional application 60/625,563, filed on Nov. 8, 2004--

Signed and Sealed this
Third Day of March, 2015

Michelle K. Lee
*Deputy Director of the United States Patent and Trademark Office*